US012066422B2

(12) United States Patent
Whalen et al.

(10) Patent No.: US 12,066,422 B2
(45) Date of Patent: Aug. 20, 2024

(54) PORTABLE SYSTEM FOR ANALYzING MICROBIAL POPULATION IN A FLUID

(71) Applicant: LUMINULTRA TECHNOLOGIES LTD., Fredericton (CA)

(72) Inventors: Patrick Andrew Whalen, Fredericton (CA); Derek Christopher Dunn, Fredericton (CA); William Dicke, Gatineau (CA); Xavier Boulerice, Ottawa (CA); David McMullin, Ottawa (CA); Michael Brown, Ottawa (CA)

(73) Assignee: LUMINULTRA TECHNOLOGIES LTD., Fredericton (CA)

( * ) Notice: Subject to any disclaimer, the term of this patent is extended or adjusted under 35 U.S.C. 154(b) by 404 days.

(21) Appl. No.: 17/288,772

(22) PCT Filed: Dec. 13, 2019

(86) PCT No.: PCT/CA2019/051812
§ 371 (c)(1),
(2) Date: Apr. 26, 2021

(87) PCT Pub. No.: WO2020/118451
PCT Pub. Date: Jun. 18, 2020

(65) Prior Publication Data
US 2021/0405012 A1   Dec. 30, 2021

Related U.S. Application Data

(60) Provisional application No. 62/779,756, filed on Dec. 14, 2018.

(51) Int. Cl.
*G01N 33/18* (2006.01)
*G01N 1/10* (2006.01)
*G01N 21/76* (2006.01)

(52) U.S. Cl.
CPC ............... *G01N 33/18* (2013.01); *G01N 1/10* (2013.01); *G01N 21/76* (2013.01)

(58) Field of Classification Search
CPC ........ C12Q 1/66; C12Q 1/008; G01N 21/763; G01N 2021/0325; G01N 21/76; G01N 1/10
(Continued)

(56) References Cited

U.S. PATENT DOCUMENTS 4,385,113 A   5/1983  Chappelle et al.
6,599,712 B1  7/2003  Sakakibara et al.
(Continued)

FOREIGN PATENT DOCUMENTS

JP   2015021906 A  *  2/2015
JP   2015021906 A     2/2015
(Continued)

OTHER PUBLICATIONS

European Patent Application No. 19895330.9, Extended European Search Report dated Aug. 25, 2022.
(Continued)

*Primary Examiner* — Eric S. McCall
*Assistant Examiner* — Timothy P Graves

(57) ABSTRACT

A system and process may be used to test water samples to measure ATP and/or estimate a microbial population, for example using an adenosine triphosphate (ATP) based assay. The system includes a device that is use in combination with single-use or disposable cartridges. The cartridge receives the water sample and is pre-loaded with one or more reagents. The device receives the cartridge and contains physical, electronic and/or mechatronic devices that interact with cartridge. One or more actions such as metering, mixing and conveying are performed automatically by elements of the device and/or cartridge. A sensor in the device
(Continued)

measures light produced in the cartridge from a reaction with ATP in the water sample. Optionally, the cartridge also contains a pre-loaded amount of ATP, which is used to provide an internal reference or calibration measurement.

27 Claims, 11 Drawing Sheets

(58) Field of Classification Search
USPC .............................. 435/288.7; 422/502, 81
See application file for complete search history.

(56) References Cited

U.S. PATENT DOCUMENTS

| | | |
|---|---|---|
| 9,222,623 B2 | 12/2015 | Wright et al. |
| 9,498,778 B2 | 11/2016 | Corey et al. |
| 9,527,077 B2 | 12/2016 | Wright |
| 9,873,120 B2 | 1/2018 | Wright |
| 2001/0038450 A1 | 11/2001 | McCaffrey et al. |
| 2006/0073537 A1 | 4/2006 | Cairns et al. |
| 2008/0182238 A1 | 7/2008 | Carins et al. |
| 2015/0322481 A1 | 11/2015 | Davenport et al. |
| 2015/0337358 A1 | 11/2015 | Driscoll et al. |
| 2017/0259268 A1 | 9/2017 | Wright |

FOREIGN PATENT DOCUMENTS

| | | | | |
|---|---|---|---|---|
| WO | 9719353 A1 | 5/1997 | | |
| WO | WO-9719353 A1 * | 5/1997 | ............... | C12Q 1/66 |
| WO | 2005097968 A1 | 10/2005 | | |
| WO | 2006134698 A1 | 12/2006 | | |
| WO | WO-2006134698 A1 * | 12/2006 | ........ | B01L 3/502715 |
| WO | 2011123064 A1 | 10/2011 | | |
| WO | WO-2011123064 A1 * | 10/2011 | ............ | B01L 3/5027 |
| WO | 2012094459 A2 | 7/2012 | | |

OTHER PUBLICATIONS

Kim, et al., "Statistical Optimization of the Lysis Agents for Gram-negative Bacterial Cells in a Microfluidic Device," Biotechnology and Bioprocess Engineering,korean Society for Biotechnology and Bioengineering, vol. 11 (4), pp. 288-292.
International Patent Application No. PCT/CA2019/051812, International Preliminary Report on Patentability dated Jun. 24, 2021.
International Patent Application No. PCT/CA2019/051812, International Search Report and Written Opinion dated Feb. 24, 2020.

* cited by examiner

PORTABLE SYSTEM FOR ANALYzING MICROBIAL POPULATION IN A FLUID

RELATED APPLICATIONS

This application is a National Stage Entry of International Application No. PCT/CA2019/051812, filed Dec. 13, 2019, which claims priority from and the benefit of U.S. patent application Ser. No. 62/779,756, filed on Dec. 14, 2018, which U.S. patent application Ser. No. 62/779,756 is incorporated herein by this reference to it.

FIELD

This specification relates to testing samples, for example of water, to measure a microbial population in the sample, for example using an adenosine triphosphate (ATP) based assay.

BACKGROUND

US Patent Application Publication No. US 2006/0073537 A1, Reagent System and Process for Adenosine Triphosphate Monitoring, describes a reagent system having a first reagent and a second reagent. The first reagent includes a high pH phosphate buffer. The second reagent includes luciferase, luciferin, a magnesium salt and an enzyme stabilizer. The reagent system may be used in a process for measuring total adenosine triphosphate (ATP) and/or dissolved extracellular ATP.

US Patent Application Publication No. US 2008/0182238 A1, Process and Apparatus for Reducing Interferences in Biochemical Assays, describes a method of conducting a biochemical assay including treating a mixture of cell sample and cell constituents solubilizing agent with an insoluble agent prior to conducting the assay. The publication also describes a device and kit for carrying out such assays.

INTRODUCTION

The following introduction is intended to introduce the reader to the detailed description to follow and not to limit or define any claimed invention.

A system and process described herein may be used to test water samples to measure one or more ATP parameters and optionally estimate a microbial population (optionally expressed as a concentration) in the sample, for example using an adenosine triphosphate (ATP) based assay.

The system includes a device that is portable, optionally hand held, in combination with one or more cartridges. The cartridge can be a single use cartridge, and the system can include a supply of multiple cartridges to perform multiple tests with the same device. The cartridge receives the water sample. The cartridge is also pre-loaded with one or more reagents. The device receives the cartridge and contains physical, electronic and/or mechatronic devices that interact with cartridge. The cartridge and/or the device include features that assist in metering a specified amount of one or more reactants or the water sample, in moving one or more reactants or the water sample, and/or in mixing one or more reactants or the water sample. In some examples, inserting the cartridge into the device causes the movement of one or more liquids in the cartridge. In some examples, an electrically powered component in the device causes the movement of one or more liquids in the cartridge. In some examples, the cartridge contains features that are moved by a user to move one or more liquids in the cartridge. A sensor in the device measures light produced in the cartridge, for example from a reaction with ATP in the water sample. Optionally, the cartridge also contains pre-loaded ATP, which may be used to provide an internal reference (i.e. calibration) measurement.

In a process described herein, an ATP measurement is made using a device and cartridge. The measurement may be of total ATP or dissolved ATP. One or more ATP measurements may be converted into cellular ATP measurement, a biomass stress index or an estimate of microbial population. The process may also include one or more actions such as metering, mixing and conveying that are performed, optionally automatically, by elements of the device and/or cartridge. The process may also include an adjustment of the measurement, which is optionally automated, based on a second measurement of ATP pre-loaded into the cartridge.

The water tested could be any aqueous fluid, including solutions or dispersions, and the device might also be used for non-aqueous fluids. For example, the device might be used to test surface water, drinking water, wastewater, organic fluids, paints, coatings, food derived liquids, plant derived liquids, or surfaces swabbed with a liquid. The device described herein is used to measure ATP but some or all of the aspects of it might be adapted or used for other tests.

In some examples, a user introduces a portion of a water sample into the cartridge and inserts the cartridge into the device. Predetermined amounts of reagents required to perform an ATP measurement are pre-loaded into the cartridge. The device and/or cartridge separate a predetermined amount of the introduced water for use in the test. After performing the test, the device and cartridge automatically perform a second measurement, used as an internal reference measurement, of a predetermined amount of ATP that was also pre-loaded into the cartridge. The device and cartridge thereby simplify the process of ATP testing by automating various steps of water sample and reagent measurement, movement and/or mixing; and, by automating the process of performing an internal reference or calibration measurement. An accurate measurement is encouraged, firstly, by avoiding human error in the measurement of very small quantities of water or reagents and, secondly, by providing an internal reference measurement.

DETAILED DESCRIPTION

Figure 1A:
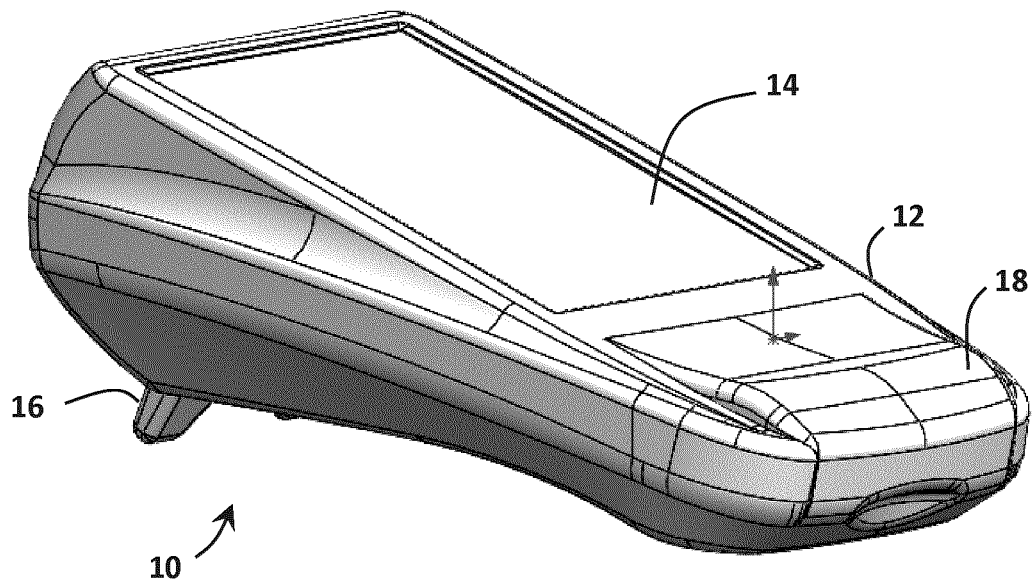
FIG. 1A is an isometric view of a portable water testing device with a door closed.

A cartridge is described herein for use with a water testing device. In some examples, the cartridge has a water sample inlet port, a sample well in communication with the inlet port, and one or more ATP assay reagents. One of the ATP assay reagents may be luciferase. The luciferase, and optionally other ATP assay reagents, may be pre-loaded into the sample well, optionally in dried form. The cartridge can have a rehydration and/or dilution reagent in communication with the sample well.

The cartridge may also have a metering channel in communication with the water sample inlet port and the sample well. An optional fill valve of the cartridge is adapted to selectively permit flow from the water sample inlet port to the metering channel, or from the metering channel to the sample well. The cartridge can also have an air port in communication with the metering channel. A lysing reagent may be pre-loaded into the metering channel, optionally in a dried form.

The cartridge may also be pre-loaded with ATP, optionally in a stabilized aqueous or dried form. The ATP may be located in a channel located between an air port and the sample well. The ATP channel may also be in communication with a lock wick. The cartridge can have a rehydration and/or dilution reagent in communication with the ATP. The same rehydration and/or dilution reagent may also be on communication with the sample well as mentioned above.

In some examples, the cartridge has one or more reservoirs each containing one or more reagents, optionally in aqueous dispersion or solution. The reagents can include, for example, a lysing reagent, a dilution and/or rehydrating reagent, or a calibration reagent. One or more of the reservoirs may be collapsible. In some examples, the cartridge has a paddle adapted to collapse the collapsible reservoir. In some examples, a reservoir is collapsed by the action of inserting the cartridge into the water testing device.

The cartridge is placed in a package for storage or shipping. The package is preferably sealed to avoid contaminating any pre-loaded chemicals with air, particularly moisture in the air. Optionally, a desiccant is included inside the package. The package is preferably opaque to avoid degrading any pre-loaded chemicals with light. In some examples the package is an opaque, optionally foil lined, plastic bag with an individual cartridge sealed inside of it. In some examples, the package is a resealable bag or box with multiple cartridges inside of it.

A water testing device for use with a cartridge as described above can contain one or more physical, electronic and/or mechatronic devices that interact with cartridge. For example, the device may have a feature such as a bearing surface or roller configured to collapse a reservoir of the cartridge when the cartridge is inserted into the device. The device has one or more sensors to measure an attribute of the water sample or a reaction involving the water sample. For example the device can have a light sensor adapted to receive light generated in the sample well of a cartridge inserted into the device, for example by way of a firefly assay used to measure ATP. In some examples the device has an air pump, which may be used to move fluids, or portions of fluids, within the cartridge.

To test a water sample, a cartridge is removed from its packaging. Water is loaded into a cartridge and the cartridge is loaded into a device. The cartridge may be pre-loaded with one or more reagents, for example when the cartridge was manufactured, or otherwise by machine or at least with the aid of manufacturing equipment. For example, one or more reagents can be providing in a dried, gel, absorbed or other stabilized form within the cartridge, or in an aqueous form in a reservoir of the cartridge. In some examples, one or more ATP assay (also called firefly assay) reagents are pre-loaded into the cartridge.

The cartridge thereby contains water to be tested and one or more reagents. At least some of the water is reacted with one or more reagents to produce a modified water sample or reaction product that can be measured. In some examples, at least some of the water in the cartridge is used in a firefly assay reaction including the one or more pre-loaded ATP assay reagents. A sensor of the device measures light produced in the cartridge due to the firefly assay reaction. The light measurements can be converted into an ATP measurement.

To make a total ATP measurement, at least some of the water sample in the cartridge, which will be involved in the firefly assay reaction, can be contacted with a cell lysing reagent pre-loaded in the cartridge. The process can include re-hydrating the one or more ATP assay reagents in the cartridge before reacting them with the water sample. The process can also include metering a selected volume from the water loaded into the cartridge for use in the firefly assay reaction. In some examples, at least some of the re-hydration, metering or other functions are performed automatically by the device. One or more fluids can be moved within the cartridge, for example, with air provided from the device, with a paddle attached to the cartridge, or by collapsing a reservoir of the cartridge by way of inserting the cartridge into the device. A second measurement can be made of light produced in the cartridge from ATP pre-loaded in the cartridge to improve the accuracy of the first measurement, for example by providing a calibration or internal reference measurement.

In some examples, a cartridge has a collapsible reservoir associated with a paddle. The paddle is hinged to the cartridge and is optionally bendable at a fulcrum. The collapsible reservoir may have a region that is engaged by the fulcrum of the paddle, which causes a portion of the reservoir in this region to be ruptured. Continued movement of the paddle, optionally involving bending the paddle about the fulcrum, crushes the remainder of the reservoir to push fluid out of the reservoir through the ruptured area of the reservoir.

In some examples, a fluid valve in a cartridge has a formed resilient flap in a chamber. The chamber is deeper than the thickness of the flap. However, the flap is formed with first and second spaced apart raised portions that can fill the depth of the chamber. Deforming the raised portions downwards creates a first pathway through the chamber above the flap. Deforming a part of the flap between the raised portion upwards creates a second pathway through the chamber below the flap. The flap has a hole in the first raised portion. One side (i.e. an upper side) of the chamber has a port over the second raised portion, and the other side of the chamber has a port under the first raised portion and a port under the second raised portion. Adding a fluid from the port in the upper side of the chamber opens the first fluid pathway over the flap from the port in the upper side of the chamber through the hole of the flap to a port on the lower side of the chamber below the hole. Adding a fluid from one of the ports in the lower side of the chamber opens the second fluid pathway below the flap between the two holes on the lower side of the chamber.

FIG. 1A shows a portable water testing device 10. The device 10 has a housing 12. The housing 12 supports a user interface 14. In the example illustrated, the user interface 14 includes a touch sensitive display. The interface 14 can receive commands through contact, which may include movement, of a finger or stylus against the display. The interface 14 can also communicate information, for example requests for commands, information on the status of a test or any of the related equipment, and/or results of tests. In the example shown, the information is communicated by way of visual display. Alternatively or additionally, commands may be received by other means such as buttons or other switches or electronic communication with another device. Alternatively or additionally, information may be communicated by other means such as lights, sounds, print-outs or electronic communication with another device. In the example shown, electronic circuitry within the housing is adapted to provide wireless (i.e. Wi-Fi and/or Bluetooth) communication with another device such as a personal computer (optionally including a smartphone, tablet, watch etc.) or a network device such as a router. Alternatively or additionally, a communication port such as a USB port or Ethernet port may be added to the device 10.

The housing 12 is preferably of a size that can be held in one hand of a human operator. For example, the housing 12 may be less than 300 nm long or less than 220 mm long, less than 150 mm wide or less than 120 mm wide, and less than 120 mm deep or less than 100 mm deep. Optionally, the housing 12 may include a foot 16, which may be movable foot. The foot 16 can be used to present the user interface 14 at a selected angle, or in two or more alternative orientations, when the device 10 is placed on a table or other surface. In the example shown, the foot 16 has an extended position as shown in FIG. 1A and a retracted position in FIG. 2.

Figure 1B:
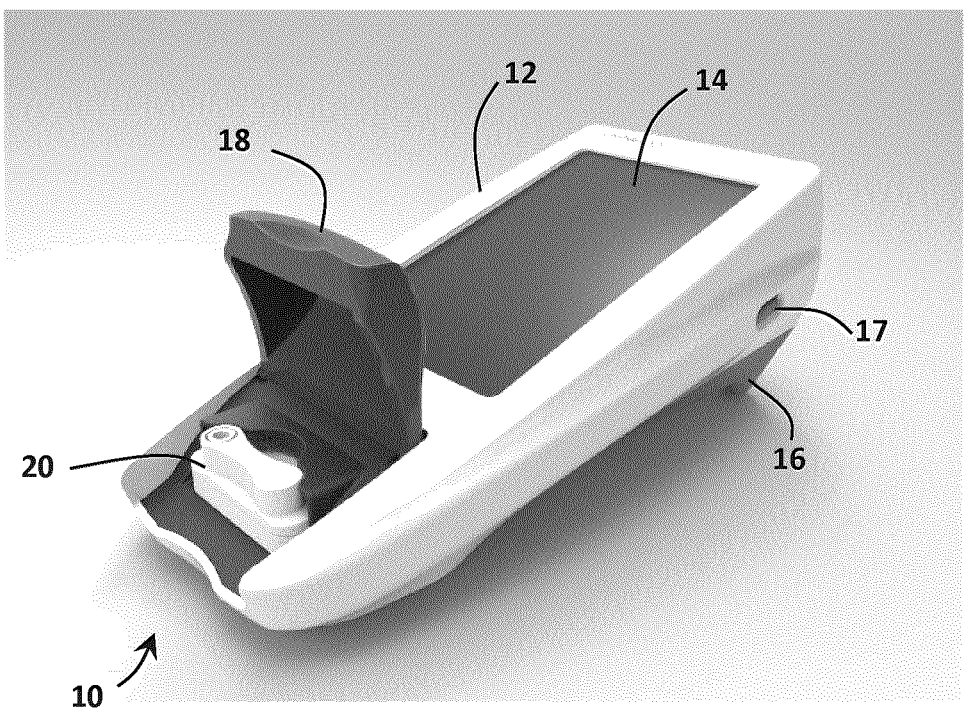
FIG. 1B is an isometric view of another water testing device with a door open.

The housing 12 also includes a door 18 that may be opened to allow the insertion of a cartridge 20 (not visible in FIG. 1, described further below) and closed to enclose the cartridge 20 in the housing 12. FIG. 1B shows another water testing device 10 with a door open. An end of the cartridge 20 is visible. The remainder of the cartridge 20 is within the device 10. In this device 10, the foot 16 is stationary. An electrical port 17, which may be a communication port and/or a battery charging port is accessible through an opening in the housing 12. In this example, the port 17 is a port for a micro USB cable used to recharge the battery 54. An on-off switch (not shown) is accessible through the housing and allows an operator to connect or disconnect the battery 54, thereby turning the device 10 on or off.

Figure 2:
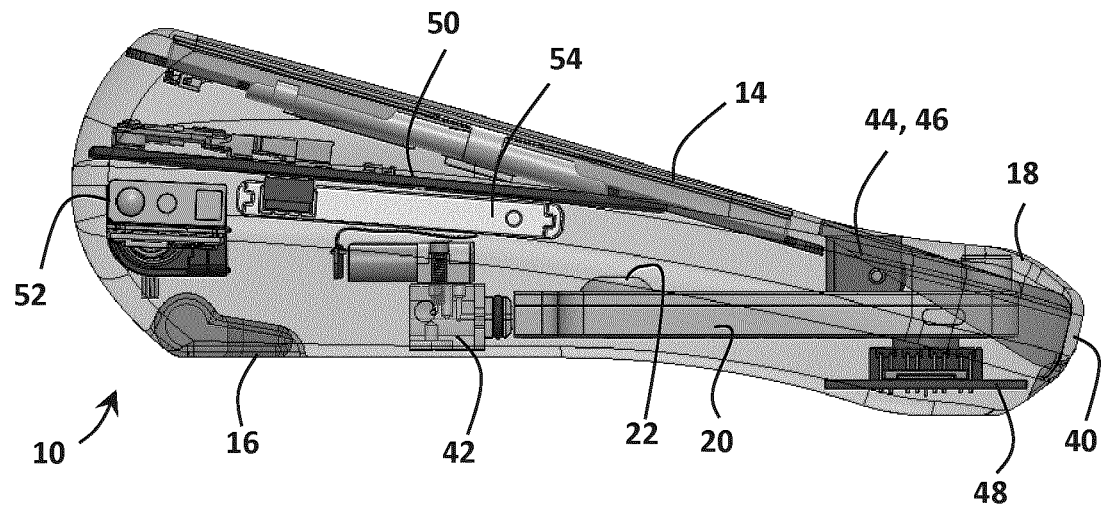
FIG. 2 is a side view of the device of FIG. 1 with one side of the housing of the device cut open and parts of a cartridge receiver removed.

FIG. 2 is a side view showing various internal components of the device 10. A light sensor 40 is provided on or connected to a first circuit board 48. The first circuit board 48 receives signals from the light sensor 42 and conveys the signals to a second circuit board 50. The second circuit board 50 is connected to and controls the first circuit board 48. As discussed further below, the light sensor 40 will provide a measurement of light emitted from a water sample in the cartridge 20, preferably over time. The light is produced by reactions according to the firefly assay, which can be correlated with a concentration of ATP in the sample.

The second circuit board 50 also controls and/or receives signals from the user interface 14, a pump assembly 42 and a scanner 52. Optionally the functions of either the first circuit board 42 and the second circuit board 44 may be provided by the other circuit board or by a smaller or larger number of circuit boards. Multiple circuit boards can be connected together by wires or ribbons of wires as required. The size and number of circuit boards can be selected to fit within the size and shape of the device 10. The device 10 is powered by a battery 54, which may be rechargeable.

Scanner 52 may be, for example, a bar code scanner or a QR code scanner. The cartridge 20 displays a code, for example a bar code or a QR code, that can be read by the scanner 52. Before being inserted into the housing 12, the cartridge 20 is placed near the scanner 52 so that the code on the cartridge 20 can be read and conveyed to the second circuit board 50. The code provides information relevant to a water test, such as the type of water sample (for example waste water, drinking water or industrial process water), the configuration of the cartridge 20 (for example the type and amount of reagents present and where they are located) and/or the measurement to be obtained. In other options, the scanner 52 may be other than a visual scanner, for example an RFID tag reader. In other options, the operator may enter some or all of the information provided by the code through the user interface 14.

In FIG. 2, a cartridge 20 has been inserted into the device 10. The cartridge 20 is removable and not part of the device 10. The cartridge 20 and device 10 collectively provide a water testing system. In the configuration shown in FIG. 2, the cartridge has been fully inserted into the device 10. One part of the cartridge 20 (the left end in the example shown) is engaged with pump assembly 42. Another part of the cartridge 20 (near the right end in the example shown) is exposed to sensor 40. Another part of cartridge 20 (the upper surface in the example shown) has passed by roller 44 (inside of the roller mount 46 visible in FIG. 2). A collapsible reservoir 22 of the cartridge 20 was compressed by the roller 44 when the cartridge 20 was inserted into the housing 20. The reservoir 22 preferably remains collapsed when in the housing 12. However the reservoir 22 is shown in an uncollapsed configuration in FIG. 2 to indicate its location when in the device 10. Optionally, there may be more than one reservoir 22.

The cartridge 20 contains one or more reagents and is loaded with a water sample before being inserted into the housing. Some movement of reagents occurs when the cartridge 20 is inserted by way of a reagent in a reservoir 22 being pressed out of the reservoir 22 by the roller 44. Additional movements, for example of the water sample and one or more reagents, are provided by the pump assembly 42, which will be discussed further below.

Figure 3:
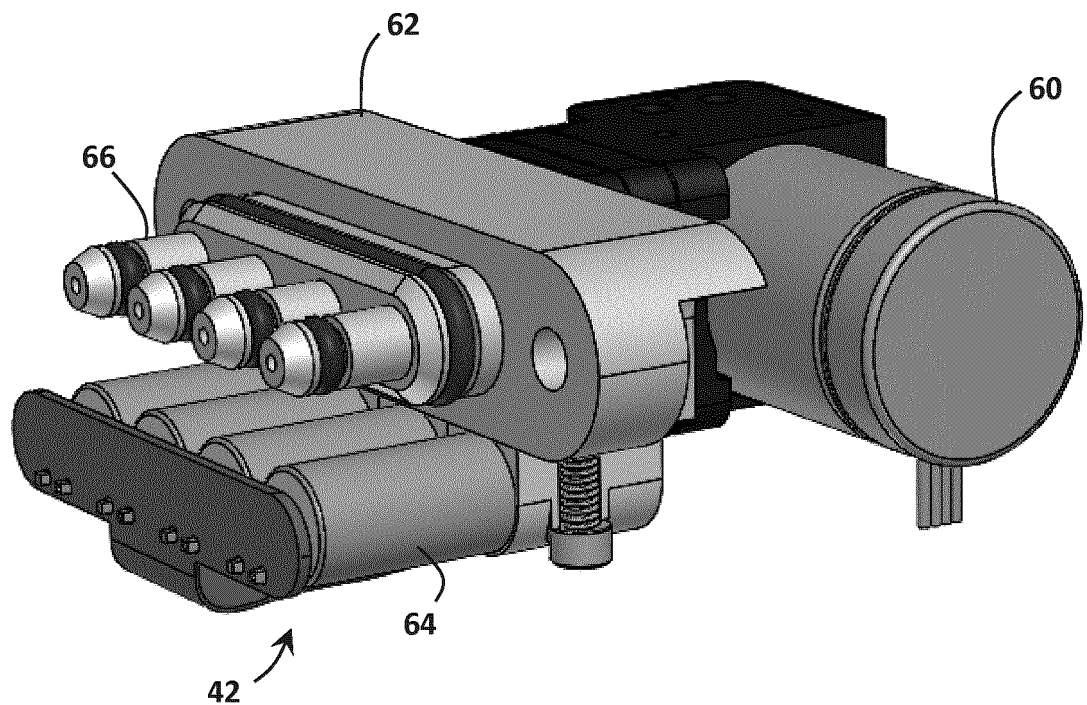
FIG. 3 is an isometric view of a pump assembly of the device of FIG. 1A.

FIG. 3 shows the pump assembly 42. The pump assembly 42 includes a pump 60, a multiple port valve 62 and solenoids 64. The pump 60, when activated, pumps air into the multiple port valve 62. Air can flow out of the multiple port valve 62 through one or more nozzles 66. In the example shown there are four nozzles 66, but there may be more or less nozzles 66. Each nozzle 66 communicates with the multiple port valve 62 through a separate passageway with a separate closure mechanism adapted to selectively close the passageway. Each closure mechanism is moved by one of the solenoids 64. By selectively activating the solenoids 64, air can be made to flow (while the pump 60 is activated) through any particular one or more of the nozzles 66.

Figure 4:
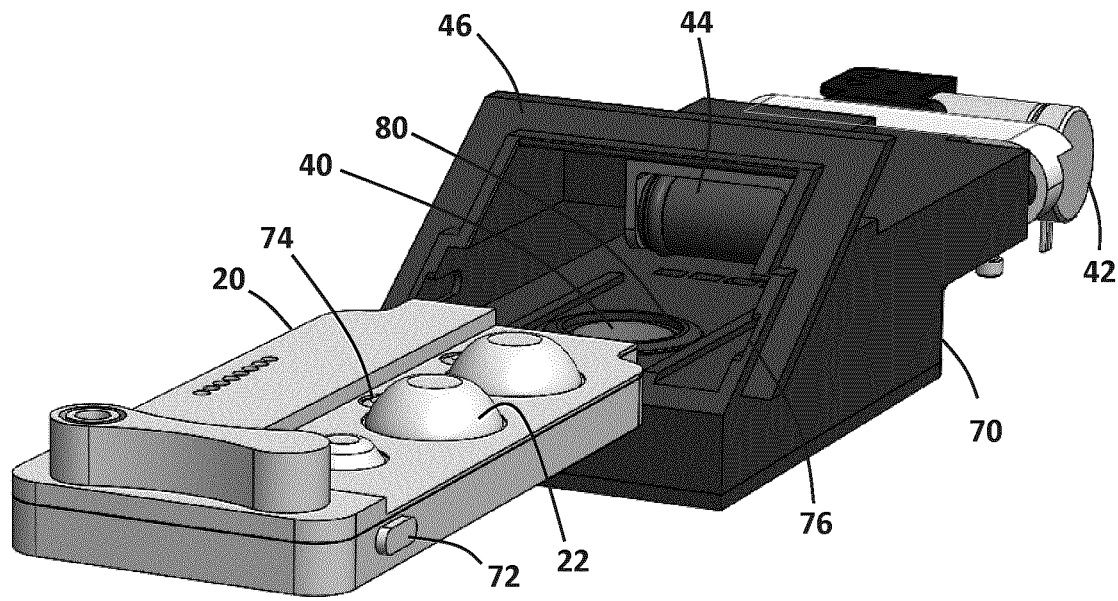
FIG. 4 is an isometric view of a cartridge receiver of the device of FIG. 1A.
Figure 5:
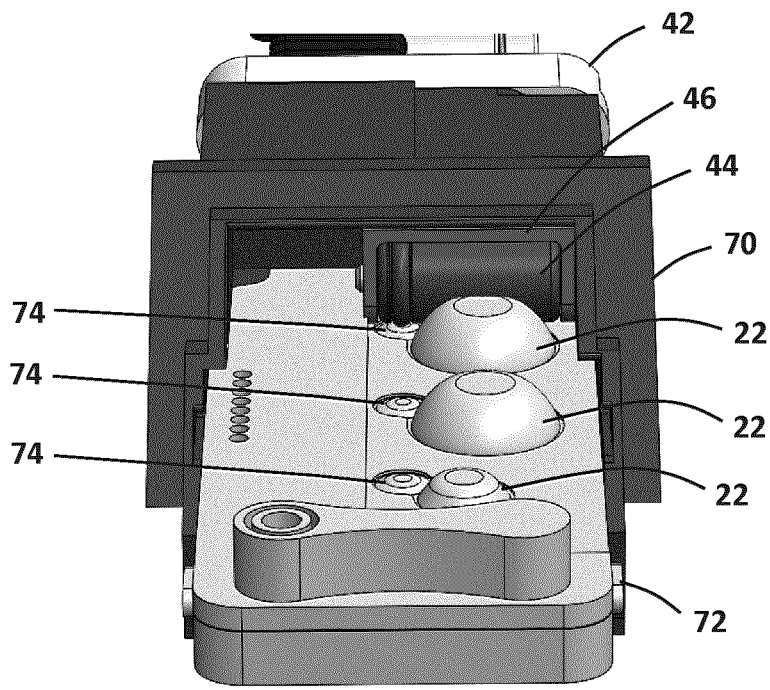
FIG. 5 is an isometric front view of the cartridge receiver of FIG. 1A with a cartridge partially inserted.
Figure 6:
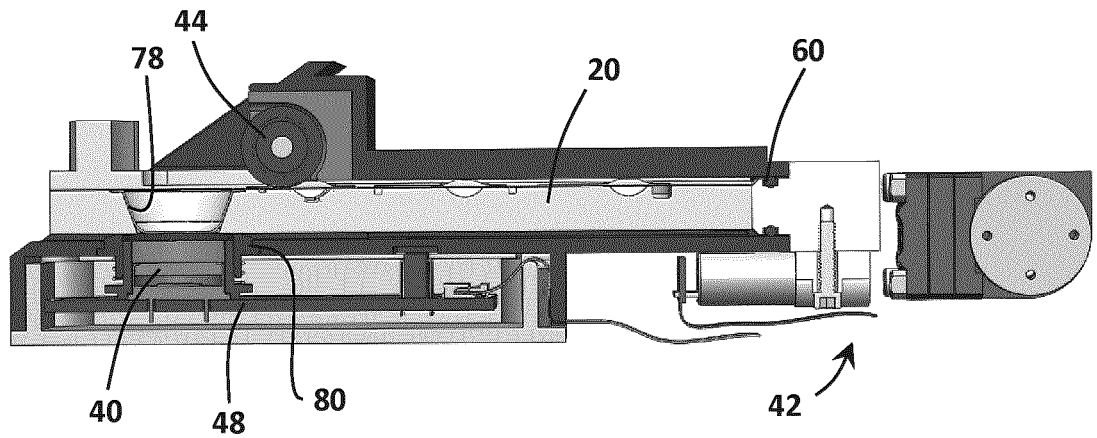
FIG. 6 is a side view of the cartridge receiver of FIG. 1A with a cartridge fully inserted.

FIGS. 4, 5 and 6 show a cartridge receiver 70. The cartridge receiver 70 is held within the housing 12. Parts of the cartridge receiver 70 were removed in FIG. 2 to allow other components to be visible. The cartridge receiver 70 provides a slot that the cartridge 20 can slide into. Stops 72 engage detents 76 in the cartridge receiver 70 to indicate when the cartridge 20 has been fully inserted. The stops 72 also prevent, by physical interference, the cartridge 20 from being inserted too far into the cartridge receiver 70.

The cartridge receiver 70 holds the pump assembly 42. When the cartridge 20 is fully inserted, the nozzles 66 of the pump assembly 42 are inserted into an end of the cartridge 20. The sensor 42 and first circuit board 48 are located within the cartridge receiver 70. When the cartridge 20 is fully inserted, a sample well 78 of the cartridge 20 is located over the sensor 40. A gasket 80 around an opening in the bottom of the slot of the cartridge receiver 70 seals against the bottom of the cartridge 20 to help prevent light from outside of the sample well 78 from reaching the sensor 40.

Each reservoir 22 of the cartridge 20 has an associated outlet with a collapsible gate 74. As the cartridge 20 is inserted into the cartridge receiver 70, the roller 54 ruptures the gates 74 and collapses the reservoirs 22. As each gate 74 is ruptured, it opens a pathway for liquid in the reservoir 22 to inter into the body of the cartridge 20. As each reservoir 22 is collapsed, the liquid contained in the reservoir 22 flows into the body of the cartridge 20. The use of a roller 54 to puncture a gate 74 and dispense a fluid from a reservoir 22, a blister pack type structure providing the gate 74 and reservoir 22, and alternative structures are described, for example, in US Patent Application Publication US20170259268A1 and U.S. Pat. Nos. 9,527,077; 9,222,623; 9,873,120; and, 9,498,778, all of which are incorporate by reference herein.

Figure 7:
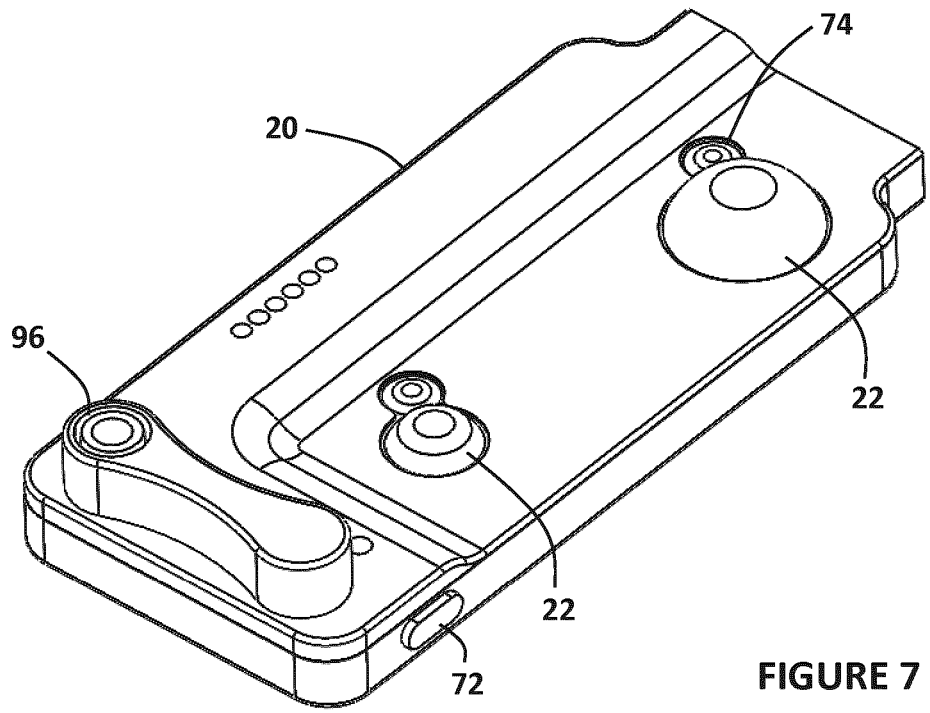
FIG. 7 is an isometric view of a cartridge that may be used with the devices of FIGS. 1A and 1B.
Figure 8:
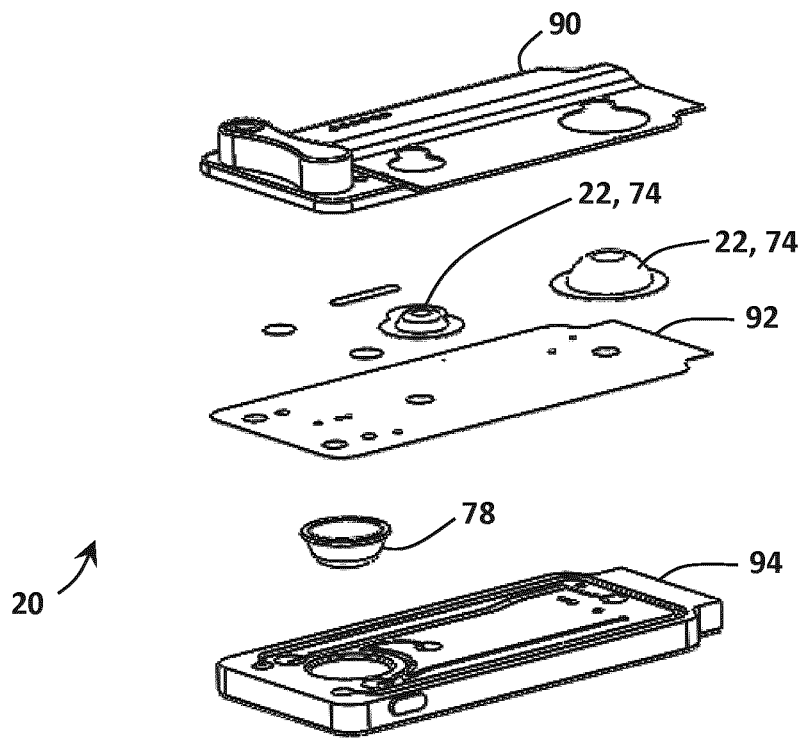
FIG. 8 is an exploded view of the cartridge of FIG. 7.

FIGS. 7 and 8 show an example of a cartridge 20. In this example, the cartridge 20 has two reservoirs 22, although in other examples there could be one, three or more reservoirs 22. Referring to FIG. 8, the cartridge 20 has a top plate 90, a middle plate 92 and a bottom plate 94. The sample well 78 is inserted into the bottom plate 94 and covered by the middle plate 92. Molded blister packages, which provide the reservoirs 22 and gates 74, are inserted between the middle plate 92 and the top plate 90. A sample inlet port 96, for example a Luer Lock port, is provided on the top plate 90. Various internal cavities, such as holes, channels and/or reservoirs, are formed in one or more of the top plate 90, middle plate 92 and bottom plate 94. The cavities are configured to facilitate a test to be performed on a water sample inserted into the cartridge 20. Some of the cavities are not visible in FIGS. 7 and 8 because they are within or on the bottom of the top plate 90, middle plate 92 or bottom plate 94. The structures shown in FIGS. 7 and 8 are optional and may be modified as required to facilitate a particular test.

Figure 9:
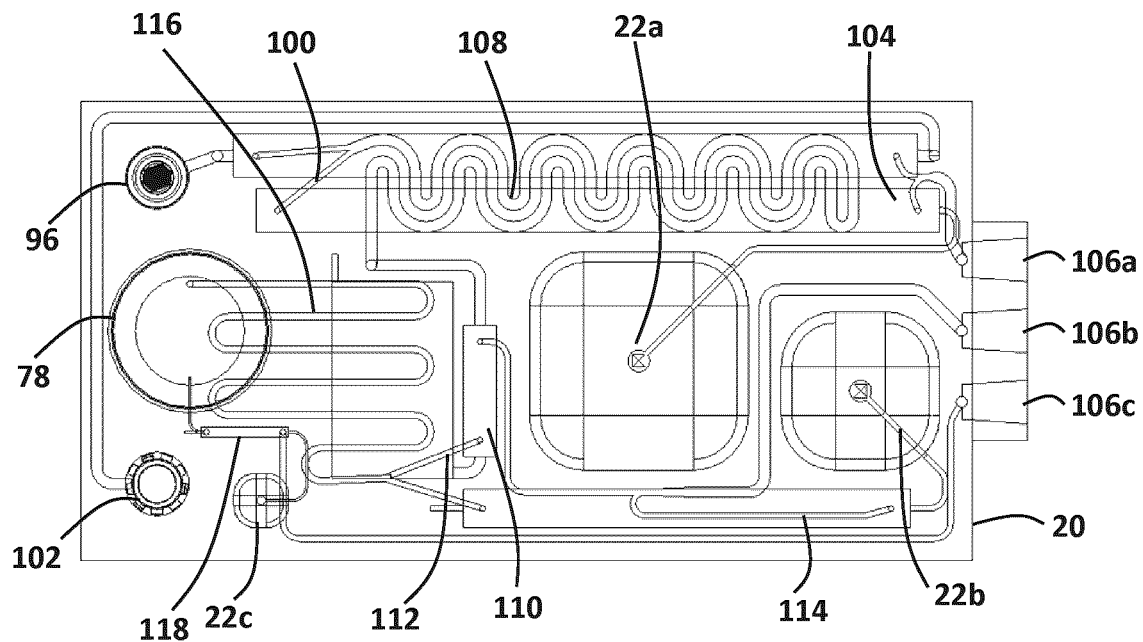
FIG. 9 is an X-ray view of another cartridge.

FIG. 9 is an "X-ray" view showing multiple planes within an example of a cartridge 20. In this example, the inlet port 96 connects to a sample-metering reservoir 100. Water in excess of the volume of the sample-metering reservoir 100 leaves the cartridge 20 through an outlet port 102. A first reservoir 22a contains a cell lysing reagent. When the cartridge 20 is inserted into the device 10, the cell lysing reagent is pushed into a lysing reagent metering reservoir 104 when the first reservoir 22a is collapsed. Cell lysing reagent in excess of the volume of the cell lysing reagent metering reservoir 104 optionally flows out through an overflow. The cell lysing reagent may be, for example, a high pH solution containing trisodium phoshate (TSP) buffer. The cell lysing reagent may optionally also include a surfactant and/or a base.

The sample-metering reservoir 100 and the cell lysing reagent metering reservoir 104 are both connected to a first air port 106a. When the cartridge 20 is inserted into the device, the first air port 106a, second air port 106b, and third air port 106c each receive a nozzle 66 of the pump assembly 42. Accordingly, air may be pumped selectively into each of the air ports 106a, 106b and 106c. When air is pumped into the first air port 106a, the contents of the sample-metering reservoir 100 and the cell lysing reagent metering reservoir 104 are pumped through a first mixing channel 108 into a lysed sample metering reservoir 110. The water sample and cell lysing reagent mix in the first mixing chamber 108 such that cells in the water sample in the lysed sample metering reservoir 110 are lysed, thereby releasing ATP from the cells. Lysed sample in excess of the volume of the lysed sample metering reservoir 110 is collected in a lysed sample overflow reservoir 112.

A second reservoir 22b contains a dilution reagent. When the cartridge 20 is inserted into the device 10, the dilution reagent is pushed into a dilution reagent metering reservoir 114 when the second reservoir 22b is collapsed. Optionally, dilution reagent in excess of the volume of the enzyme solution metering reservoir 114 flows out through an overflow. When air is pumped into the second air port 106b, the dilution reagent in the dilution reagent metering reservoir 114 and the lysed sample in the lysed sample metering reservoir 110 are pushed through the second mixing channel 116, wherein they are mixed, and into the sample well 78. The dilution reagent includes water, for example de-ionized water. If the water sample is lysed with a high pH buffer, the dilution reagent may also include a pH reducing agent.

The sample well 78 includes one or more ATP assay reagents, which include ATP enzyme (i.e. luciferase, which may be native or recombinant luciferase), luciferin, optionally magnesium (typically as a magnesium salt) and optionally a buffer with a pK that is near the optimum pH for activity of luciferase. Optionally, one or more of the magnesium salt, buffer and luciferin may be provided in the dilution reagent. The ATP assay reagents in the sample well 78 may be dried or in other forms such as a gel or adsorbed liquid. Optionally, the luciferase may be immobilized on the sample well 78. The ATP assay reagents in the sample well 78 are rehydrated when the diluted and optionally lysed water sample reaches the sample well. ATP in the water sample is measured according to the firefly assay. In particular, the ATP (excluding cellular ATP if the cells are not lysed) reacts with oxygen and luciferin, under the influence of luciferase and magnesium ions, to produce by-products and light. The light is detected in by the sensor 40, which records the emission of relative light units (RLU) over time. The signals recorded by the sensor may be analysed in a computing chip of the second circuit board 50 or transmitted to another computer for analysis.

Alternatively, the dilution reagent may be pushed directly into the sample well 78 without first mixing with the water sample. In this case, the dilution reagent may rehydrate the ATP assay reagents in the sample well 78 before the water sample is added. In this case, the water sample is also added to the sample well 78 separately. Mixing of the metered portion of the water sample (optionally lysed), dilution reagent and ATP assay reagents may occur by diffusion and/or by the force of the water sample entering the sample well 78.

A third reservoir 22c contains a calibration reagent. When the cartridge 20 is inserted into the device 10, the calibration reagent is pushed into a calibration reagent metering reservoir 118 when the third reservoir 22c is collapsed. Optionally, calibration reagent in excess of the volume of the calibration solution metering reservoir 118 flows out through an overflow. When air is supplied to the third air port 106c, calibration reagent flows from the calibration solution metering reservoir 118 into the sample well 78. The calibration reagent results in an increase in the amount of light generated in the sample well 78. A second reading (or continuation of the first reading if light) is taken with the sensor 40 to determine the amount of additional light generated, preferably over time. The calibration reagent may be a stabilized ATP solution containing a known amount or concentration of ATP.

A computing device on the second circuit board 50 uses both light measurements to determine a concentration of ATP in the water sample. The concentration of ATP in the water sample may be converted, optionally in combination with one or more additional tests (for example a test with a cartridge 20 not having a lysing solution) into an estimate of the concentration of microorganisms in the water sample. The device 10 may store the results of tests with multiple cartridges 20, may perform calculations based on the results of tests with multiple cartridges 20, and may present data in the form of, for example, total, dissolved or cellular (total-dissolved) ATP concentration, estimated microbial concentration or a biomass stress index (dissolved ATP as a percentage of total ATP). Alternatively the device 10 may transmit the readings from the sensor, with or without modification, to another computing device for analysis. The results of the analysis may be transmitted back to the device 10 for display or reviewed on another display device.

The flow of liquids moved by air in unintended directions can be inhibited, for example, by one or more of automatic one-way valves, controlled valves, air wicks, air (i.e. bubble) locks, and physical collapsing of the reservoirs 22.

An example of a process for testing a water sample will be described below. This example assumes that a human operator is performing the test. Optionally, the test process may be modified so that it can be performed by an automatic or robotic operator connected to the device 10.

In a process for testing a water sample, an operator collects a sample of the water to be tested. Depending on the source of the water, some sample preparation steps may be required. For example, excess solids may be removed, the sample may be heated or cooled to be closer to room temperature, the pH may be adjusted, or certain solutes may be removed. A portion of the sample is drawn into a syringe.

The operator turns on a power button of the device 10. A program within the second circuit board 50 will optionally go through various initialization routines and then provides instruction to the operator on next steps through the user interface 14. The second circuit board 50 may also request and record other information through the user interface 14 or other means such as a date and time, location, source of the water sample, identity of the operator, or an identification number to be given to the test.

The operator selects a cartridge 20, optionally from a set of cartridges 20 of different types adapted to different tests (for example a total ATP test or a dissolved ATP test) or for use with samples drawn from different sources of water. The cartridge 20 is removed from a package and placed in front of the device 10. The 52 scanner 52 reads a code, such as a QR code, on the cartridge 20. The scanner 52 transmits the code to the second circuit board 50, which then operates the device 10 according to applicable programming as determined by the code.

The syringe holding the water sample is connected to the inlet port 96 of the cartridge, for example by a tapered (i.e. Luer Lock) connection. The plunger of the syringe is pressed to push the water sample into the cartridge 20.

The operator opens the door 18 of the device 10. Optionally, a shutter over the sensor 40 may close automatically (for example by way or a solenoid or mechanical linkage) when the door 18 opens to protect the sensor 40 from external light. The operator inserts the cartridge 20 into the device 10 until the stops 72 engage the detents 76 in the cartridge receiver 70. Proper seating of the stops 72 in the detents 76 can be determined by the operator visually or by physical resistance. With the cartridge 20 seated in the device 10, the bottom of the sample well 78 (which is clear) will be located over the sensor 40. As the cartridge 20 is inserted, the roller 44 opens the gates 74 and collapses the reservoirs 22 of the cartridge 20. Fluids such as reagents are thereby conveyed from the reservoirs 22 into their corresponding reservoirs in the cartridge 20. The operator closes the door 18. A shutter (if any) over the sensor 40 automatically opens with the door 18 is closed.

The further steps described may occur automatically, for example under the control of the second circuit board 50. The steps may be initiated, for example, by closing the door 18 with a cartridge 20 inserted or by a command issued by the operator through the user interface 14. The pump assembly 42 uses air supplied selectively through nozzles 66 into air ports 106 of the cartridge 20 to move liquids within the cartridge 20. Movement of two or more liquids through a channel in the cartridge 20 may be used to mix the liquids (including any dispersed or dissolved elements). Hold times may be provided to allow reactions to continue after mixing if required. A mixture of water sample and one or more reagents, and separately a calibration reagent, are delivered to the sample well 78 for measurement by the sensor 40. Mechanisms, such as vents, valves or membranes, within the cartridge 20 allow excess air to be released from the cartridge 20 to prevent leaks and bubbles within the cartridge. In some examples, a hydrophobic membrane allows air to escape even when the membrane is exposed to water as bubbles can be forced through the pores of the membrane. In some examples, a hydrophilic membrane (also called a wick lock) act as a vent to atmosphere until the membrane contacts a liquid, after which air cannot pass through the membrane.

Light is created by chemical reactions in the sample well 78 according to the firefly assay (alternatively called ATP assay) reaction. The sensor 40 measures the intensity of the light emitted from the sample well 78 over time. Optionally, a measurement may be taken when only the water sample or a calibration solution is present and active in the reaction or one of the measurements may be taken when at least parts of both the water sample and the calibration solution are present and at least partially active. The measurements are converted from an analog signal produced by the sensor 40 to a digital signal in the first circuit board 48 and the digital signal is conveyed by wire to the second circuit board 50. The circuit board 50 may perform calculations to convert the measurements into an output, such as an ATP amount or concentration, estimate of microbial concentration or biomass stress index. The output is presented to the operator through the user interface 14. Optionally, some or all of the calculations, and/or additional outputs, may be provided by one or more additional computers with communication links to the device 10. Optionally, the device 10 may transmit outputs, and other records of the test, to another computer.

Figure 10:
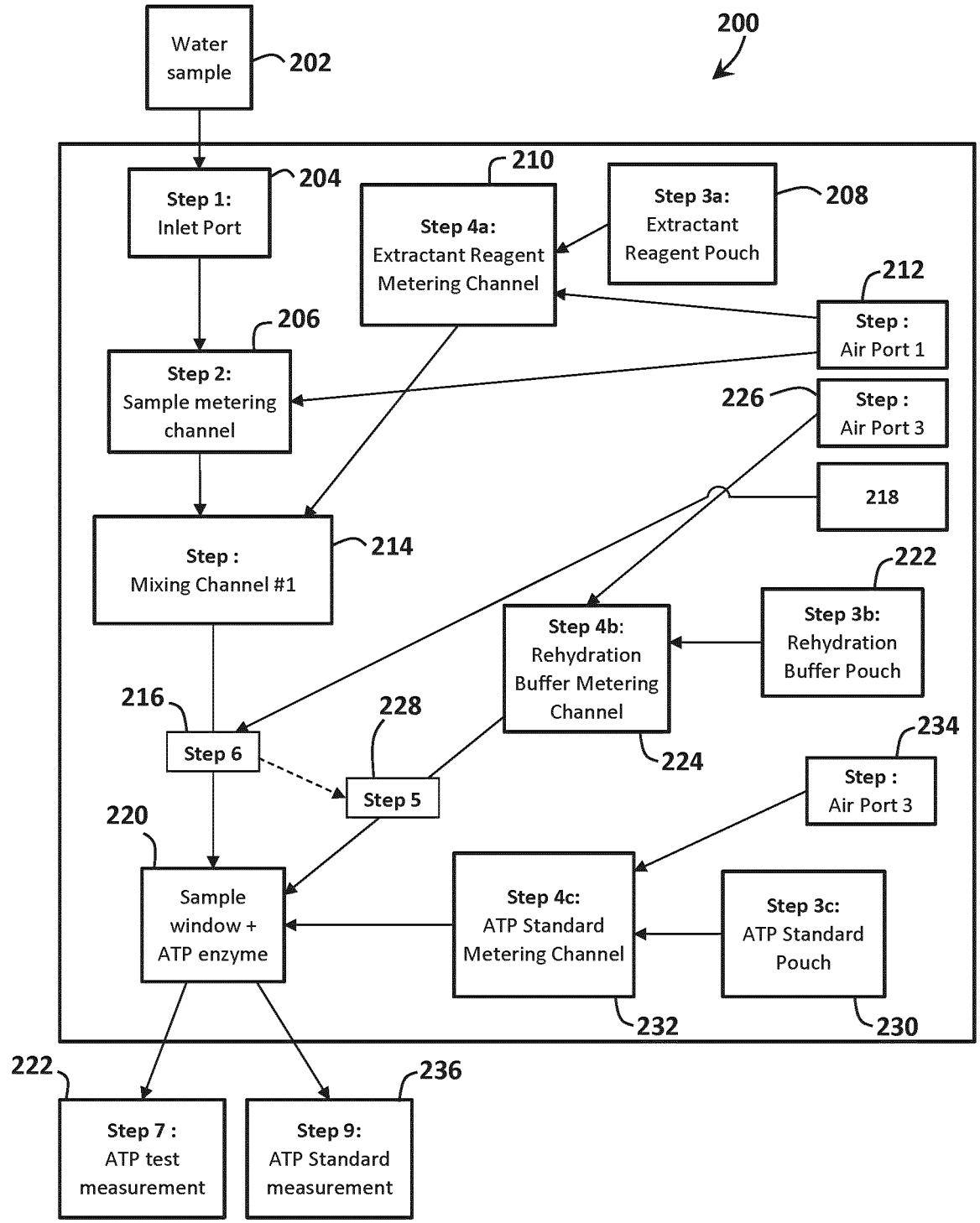
FIG. 10 is a schematic diagram of an example of a test process.

FIG. 10 shows an example of a test process 200. The steps will be numbered and discussed sequentially below, but the steps do not necessarily have to follow the order of the step numbers or description below.

In step 202, a water sample is collected. Optionally, step 202 may also include one or more sample preparation steps such as filtration, de-oiling or de-flocculating. In step 204, the water sample is loaded into the cartridge 20. In step 206, the water sample is optionally metered, i.e. a specified volume of the water sample is extracted from the total volume of water sample that was loaded into the cartridge 20.

In step 208, an extractant (i.e. cell lysing) reagent is loaded into the inside of the cartridge 20, for example by compressing a reservoir 22. In step 210, a specified volume of the extractant reagent is optionally metered and separated from the total volume of extractant reagent that was loaded into the cartridge 20. In step 212, the metered volume of extractant reagent and the metered volume of water sample are conveyed to a mixing channel. In step 214, the metered volume of extractant reagent and the metered volume of water sample are mixed, for example by further conveying them though a mixing channel. In step 216, a volume of the mixture (lysed water sample) is metered. In step 218, the metered volume of the mixture is conveyed to a sample well. In step 220, the metered volume of mixture reacts with one or more ATP assay reagents in the sample well.

In step 222, a rehydration (and/or dilution) reagent, for example deionized water optionally with a buffer or pH adjusting agent, is loaded into the inside of the cartridge 20, for example by compressing a reservoir 22. In step 224, a specified volume of the rehydration reagent is optionally metered and extracted from the total volume of rehydration reagent that was loaded into the cartridge 20. In step 226, the metered rehydration reagent is conveyed to the sample well. The rehydration reagent rehydrates (i.e. dissolves) a dried amount of one or more ATP assay reagents that were pre-loaded in the sample well. The ATP assay reagents in the sample well are preferably re-hydrated before the water sample is added to the sample well. Optionally, one or more of the ATP assay reagents, but typically not luciferase, may be included in the rehydration reagent.

In this example, the one or more ATP assay reagents such as luciferase are pre-loaded (for example in a dried form) in the sample well. The water sample and the ATP assay reagents may be mixed spontaneously when the water sample is added to the sample well, optionally aided by turbulence formed when the water sample is added to the sample well. In other examples, some or all of the compounds required for the firefly assay may be pre-loaded in a dried form in the rehydration reagent metering chamber. A hold time may be provided, if required, to allow the compounds to dissolve into the rehydration reagent. In other examples, the rehydration reagent and water sample (with or without cell extractant reagent) may be pre-mixed in optional step 228, for example by conveying the rehydration reagent and water to the sample well together through a mixing channel. In this case, steps 224 and 218 may occur at least in part together or be combined into a single step. In another option, one or more compounds may be pre-loaded into a water sample and rehydration reagent mixing channel.

In step 222, a measurement is made of the amount of light produced in the sample well, which is an amount of light produced by the reaction of ATP in the water sample with luciferin and oxygen, catalysed by luciferase and magnesium ions.

Steps 208, 210, the part of step 212 operating on the extractant reagent, and steps 214-218 are optional and used only when ATP inside of cells (as opposed to only ATP dissolved in water outside of the cells) is to be extracted from the cells and included in the measurement (producing a total ATP measurement). Where a measurement of only the ATP dissolved in water outside of the cells is desired, the metered volume of water sample is conveyed directly to the sample well for mixing with one or more ATP assay reagents such as luciferase in the sample well at step 220. A measurement of ATP in the cells (cellular ATP) can be obtained by subtracting a dissolved ATP measurement from a total ATP measurement. An estimate of microbial population or concentration can be provided based on a total ATP or cellular ATP measurement.

Steps 230 to steps 236 are used to calibrate or improve the ATP measurement by providing a reference standard including a known amount of ATP. In step 230 a calibration reagent is loaded into the inside of the cartridge 20, for example by compressing a reservoir 22. In step 232, a specified volume of the calibration reagent is optionally metered and extracted from the total volume of calibration reagent that was loaded into the cartridge 20. In step 234, the metered calibration reagent is conveyed to the sample well. The metered calibration reagent contains ATP that reacts with excess ATP enzyme in the sample well, thereby increasing the amount of light produced. In step 236, a measurement is made of the amount of light produced in the sample well, preferably over time, which is an amount of light produced by the reaction of ATP in the calibration reagent.

In the example above, steps involving the movement of liquid in the cartridge 20 can be performed by blowing air through metering channels containing the liquid. The metering channels discharge excess fluid by overflow. In other examples, the cartridge may contain pumps, such as peristaltic pumps or other microfluidic pumps, that move and/or meter fluids.

US Patent Application Publication No. US 2006/0073537 A1, Reagent System and Process for Adenosine Triphosphate Monitoring, and US Patent Application Publication No. US 2008/0182238 A1, Process and Apparatus for Reducing Interferences in Biochemical Assays, are incorporated herein by this reference to them. The reagents and other fluids used with the device 10 and cartridge 20 may be as described in these publications.

Figure 11:
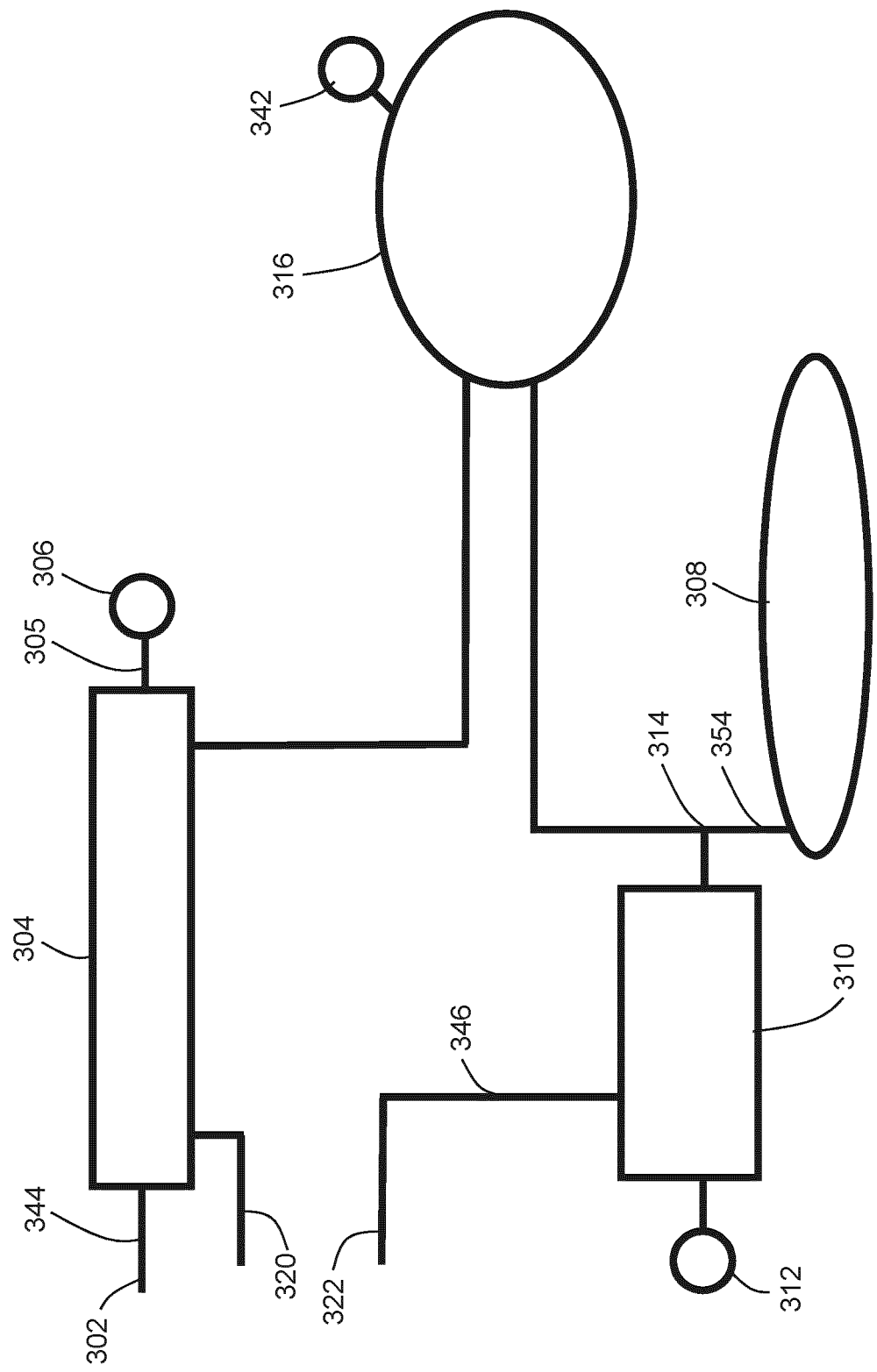
FIG. 11 is a schematic diagram of another example of a cartridge.
Figure 12:
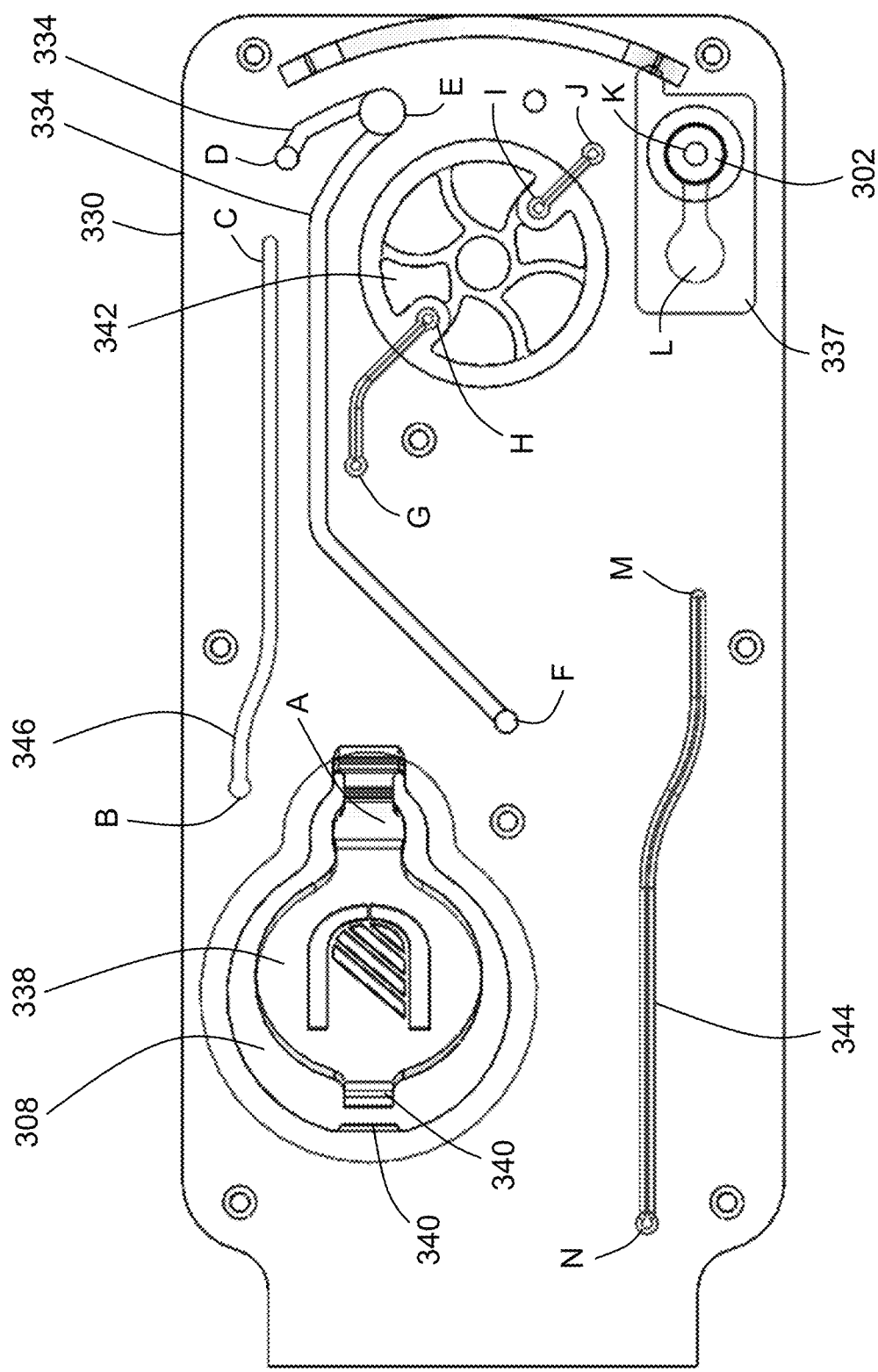
FIG. 12 is a plan view of the top of an exemplary cartridge according to FIG. 11.
Figure 13:
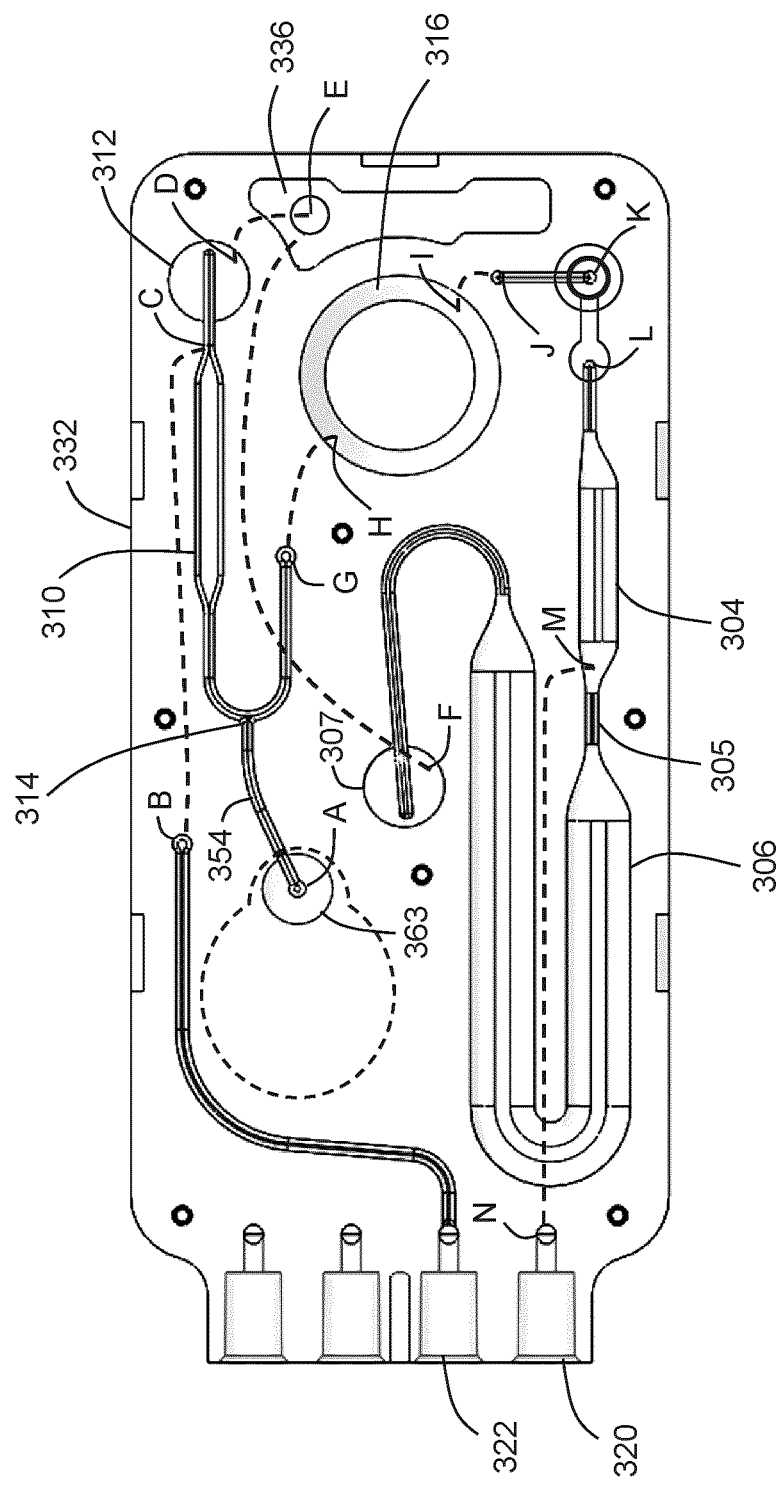
FIG. 13 is a plan view of the bottom of the cartridge of FIG. 12.

FIG. 11 shows another cartridge 300 schematically, or by way of its process flow. The cartridge 300 is used with a device 10 as described above. A top plate 330 of an exemplary cartridge 300 according to FIG. 11 is shown in FIG. 12. A bottom plate 332 of the exemplary cartridge 300 is shown in FIG. 13. Dashed lines in FIG. 13 show the approximate location of connecting features of the top plate 330. Upper case letters in FIGS. 12 and 13 indicate parts of the top plate 330 that connect to parts of the bottom plate 332. For example, area "A" on top plate 330 connects to area "A" on bottom plate 332. A method of using the cartridge 300 and some of its features will be discussed below, but the steps do not necessarily have to follow the order of the description below and functionally equivalent mechanical means may be substituted for parts described below. To the extent that no inconsistency is apparent, details of the cartridge 20 can be applied to the cartridge 300 and details of the cartridge 300 can be applied to the cartridge 20.

The user collects a water sample, for example from an industrial process, a water or wastewater treatment system, or the environment. Optionally, one or more sample preparation steps may be performed on the sample before the water sample is loaded into the syringe. For example, excess solids may be removed, the sample may be heated or cooled to be closer to room temperature, the pH may be adjusted, certain solutes may be removed, or the water may be filtered, de-oiled, or de-flocculated. A portion of the water sample is drawn into a syringe. The user connects the syringe to port 302 of the cartridge 300 and depresses a plunger of the syringe to inject a portion of the water sample into the cartridge 300. Optionally, the syringe and the port 302 may have corresponding fittings, such as a tapered, threaded or Luer Lock fittings.

The injected water sample flows from the port 302, through a fill valve 302, and through an extractant channel 304 within the cartridge 300. The volume of the extractant channel 304 is less than a specified amount of water that the user is instructed to inject into the cartridge 300 from the syringe. Excess water sample overflows the extractant channel 304 through a constriction 305 into an overflow channel 306. If the user tries to inject more than the specified volume of water sample, a lock wick 307 connected to the end of the overflow channel 306 becomes wet and provides increased resistance to further injection. This sends a haptic or tactile signal to the user to stop injecting water into the cartridge 300. Excess water passing through the lock wick 307 flows through a lock wick overflow channel 334 to a lockwick overflow chamber 336. A predetermined amount of the water sample is retained in the extractant channel 304. In this way, the extractant channel 304 acts as a metering channel and the user is not required to carefully inject an exact amount of water sample into the cartridge 300. Instead, the volume of the extractant channel 304 determines how much of the water sample is involved in reactions in the cartridge 300.

The extractant channel 304 has a specified amount an extractant (i.e. cell lysing) reagent pre-loaded into it before the water sample is added. Preferably, the extractant reagent is loaded into the extractant channel 304 when the cartridge 304 is manufactured. In this way, the user is not involved in measuring an amount of the extractant reagent. The extractant reagent may be present in the extractant channel 304 as a dried powder or other solid, as a gel, as a liquid in an absorbent material or in another suitable form. The extractant reagent and the portion of the water sample that does not pass through the constriction 305 mix in the extractant chamber 304. Optionally, a proportional amount of extractant reagent can also be provided in the overflow channel 306 to reduce the diffusion of substances in either the extractant chamber 304 or the overflow chamber 306 through the constriction.

The extractant reagent opens cells in the water sample. ATP is thereby released from the cells into solution with the water sample. The cell lysing reagent may be, for example, a high pH solution containing trisodium phosphate (TSP) buffer. The cell lysing reagent may optionally also include a surfactant and/or a base. A lysed water sample of known volume is thereby created in the extractant chamber 304. The water sample can be injected into the cartridge 300 before or after inserting the cartridge 300 into the device 10. If the water sample is injected into the cartridge 300 while the cartridge 300 is in the device 10, a first air port 320 connected to the extractant channel 34 will be block by parts of the device 10. However, if the water sample is injected into the cartridge 300 before inserting the cartridge 300 into the device 10, the first air port 320 is temporarily sealed, for example with a plug or piece of tape. The seal is removed from the first air port 320 before the cartridge 300 is inserted into the device 10. Optionally, a specified wait period is imposed by the user or automatically by the device 10 after injecting the water sample into the cartridge 300 before moving the lysed water sample out of the extractant channel 304 (as discussed further below) to give adequate time to open cells in the water sample.

The cartridge 300 also contains a rehydration (and/or dilution) reagent in a rehydration reagent pouch 308. The dilution reagent includes water, for example de-ionized water. If the water sample is lysed with a high pH buffer, the dilution reagent may also include a pH reducing agent.

The user opens a seal in the rehydration reagent pouch 308 and squeezes the rehydration reagent pouch 308 to push a predetermined amount of the rehydration reagent out of the rehydration agent pouch 308 and into the rest of the cartridge 300. Optionally, the action of squeezing the rehydration reagent pouch 308, for example by depressing paddle 338, may also open the seal in the rehydration reagent pouch 308. Preferably the rehydration reagent pouch 308 and/or the cartridge 300 are configured such that a selected amount of rehydration reagent is pushed out of the rehydration reagent pouch 308 by way of the user making a defined motion, for example depressing the paddle 338 until a click lock 340 between the paddle 338 and the top plate 330 is engaged. Optionally, the essentially the entire contests of the rehydration reagent pouch 308 are pushed out.

In the example shown, the rehydration reagent pouch 308 is squeezed before inserting the cartridge 300 into the device 10. The second air port 322 is temporarily sealed, for example with a plug or piece of tape. The seal is removed from the second air port 322 before the cartridge 300 is inserted into the device 10. Optionally, a specified wait period is imposed by the user or automatically by the device 10 after squeezing the rehydration reagent pouch 308 to give adequate time for rehydration as described below to occur. Optionally, seals over the air ports 320, 332 are provided by a tear-away portion of a label on the cartridge 300. In another option, the air ports 330, 332 can have one way valves between them and point C and M of the cartridge 300. A permanent part of the label can include a bar code or QR code to be scanned by the device 10. However, the label should not cover any vents or other ports of the cartridge 300 unless these parts of the label can also be removed by the user before the cartridge 300 is inserted into the device 10.

The rehydration reagent flows to a T-junction and separates into two portions. A first portion of the rehydration reagent flows into a calibration reagent chamber 310. An outlet of the calibration reagent chamber has a lock wick 312 connected by a lock wick overflow channel 334 to the lock wick overflow chamber 336. The lock wick 312 allows air to pass through it while the lock wick 312 is in an initial dry state. However, after the rehydration reagent wets the lock wick 312, the lock wick 312 inhibits the flow of water through it. An aqueous calibration reagent forms in the calibration reagent chamber 310.

A second portion of the rehydration reagent flows into a sample well 316. In this example, the bottom plate 332 is molded from a clear plastic and the sample well 316 is a depression molded into the bottom plate. A hydrophobic membrane vent 342 is provided in the top plate 330 over the sample well 316 to inhibit leakage from the sample well 316. The calibration reagent chamber 310 fills before the sample well 316 is full. After the lock wick 312 downstream of the calibration reagent chamber 310 becomes wet, most of the rehydration reagent still flowing from the rehydration reagent pouch 308 is directed into the sample well 316. The volume of the second portion entering the sample well 316 is essentially the volume of rehydration reagent pushed out of the rehydration reagent pouch 308 less the volume of chambers and pathways in the cartridge 300 between the rehydration reagent pouch 308, the lock wick 312 and sample well 316. Some water passes through the lock wick 312 but this amount of water is small and can be ignored. Alternatively, the exact amount of rehydration reagent reaching the sample well 316 can be determined by modeling or tests of the cartridge 300.

The first portion of the rehydration reagent rehydrates (i.e. dissolves) a reference standard including a known amount of dried ATP that has been pre-loaded into the calibration reagent chamber 310. The second portion of the rehydration reagent rehydrates (i.e. dissolves) one or more ATP assay reagents such as luciferase that are pre-loaded in the sample well 316. Alternatively, the ATP assay reagents are present in the sample well 316 in a gel, absorbed liquid or other form. The ATP reagents are preferably re-hydrated before the lysed water sample is added to the sample well.

The cartridge 300 is inserted into the device 10. The water sample is injected into the cartridge 300 or has not been previously injected into the cartridge 300. Door 18 of the device 10 is closed. Inserting the cartridge 300 into the device connects the first air port 320 and second air port 322 to nozzles 66 of the pump assembly of the device 10. The device 10 causes a selected amount of air to be released into the first air port 320. An air path 334 directs air from the first air port 320 to the extractant channel 304 just upstream (in the direction of water sample injection) of the constriction 305. The constriction 305 assists the air in separating the lysed water in the extractant channel 304 from the remaining part of the water sample. The air moves the lysed water sample from the extractant channel 304, through the fill valve 337 and into the sample well 316.

The lysed water sample and the ATP assay reagents may be mixed spontaneously when the lysed water sample is added to the sample well 316, optionally aided by turbulence formed when the water sample is added to the sample well 316. A hold time may be provided, if required, to allow the lysed water sample to react with the ATP assay reagents in the sample well 316. The device 10 makes measures the amount of light produced in the sample well 316, which is an amount of light produced by the reaction of ATP in the lysed water sample with luciferin and oxygen, catalysed by luciferase, and optionally magnesium ions pre-loaded into the sample well 316 or added with the rehydration reagent. The measurement indicates total ATP in the sample. Optionally (after a calibration or reference measurement described below) another cartridge can be made that is similar to cartridge 300 but without an extractant reagent. A measurement of a second water sample from the same source as the first water sample is loaded into this cartridge and used to determine the dissolved (i.e. non-cellular or extra-cellular) ATP. Subtracting dissolved ATP from total ATP gives a measurement of cellular ATP. The ATP measurements may be converted into, for example, ATP concentrations, a biomass stress index, or an estimate of microbial population or concentration.

To improve the accuracy of the ATP measurement, the device 10 releases a selected amount of air into the second air port 322. Air travels from the second air port 322, through a second air path 346 to the downstream end of the calibration reagent chamber 310. The air pushes the rehydrated calibration reagent from the calibration reagent chamber 310 back to the T-junction 314. The collapsed rehydration reagent pouch 308 blocks any flow back into it, so the rehydrated calibration reagent is directed into the sample well 316. The calibration reagent contains ATP that reacts with excess ATP assay reagents in the sample well 316, thereby increasing the amount of light produced in the sample well 316. Another measurement is made of the amount of light produced in the sample well 316, preferably over time, to determine an amount of light produced by the reaction of ATP in the calibration reagent. The device 10 uses this information to refine a calculation of how much ATP was present in the water sample.

The cartridge 300 is assembled by placing the rehydration reagent pouch 308, a tape gasket, a piece of silicone that provides a moving part of fill valve 337 and the wick locks 307, 312, between the top plate 330 and the bottom plate 332. The plates 330, 332 are attached to each other. The membrane vent 342 is placed on the top plate 330.

Figure 14:
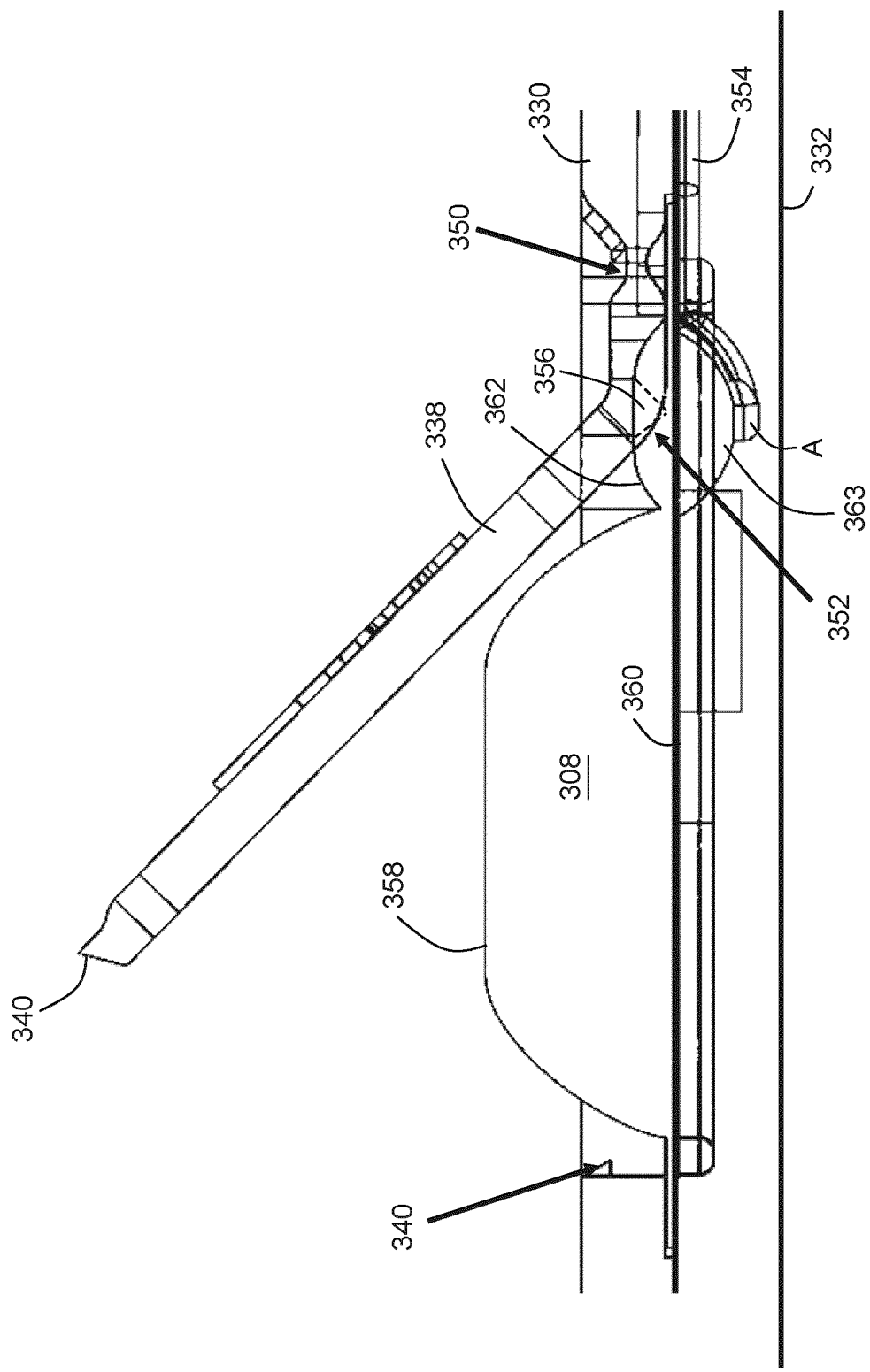
FIG. 14 is a side view of a pouch crushing part of the cartridge top of FIG. 13.

Referring to FIG. 14, the rehydration reagent pouch 308 is a collapsible reservoir, in this example having a first portion 358 and second portion 362. The first portion 358 and the second portion 362 are each blisters molded into a plastic sheet connected to a base 360. The base 360 may be made, for example, of a foil. The rehydration reagent pouch 308 is inserted into an opening in the top plate 330. Flanges of the rehydration reagent pouch 308 are contained between the plates 330, 332. The paddle 338 is a part of the top plate 330 movable through a hinge 350, for example a live hinge. In a shipping position, the paddle 338 is rotated to the right about the hinge 350 relative to the position shown in FIG. 14 so that that paddle 338 is folded back over onto the top plate 330 and does not contact the rehydration reagent pouch 308. In an intermediate position shown in FIG. 14, a fulcrum 352 of the paddle 338 crushes the second portion 362 of the rehydration reagent pouch 308. In FIG. 14, the paddle 338 is shown in this intermediate position but the second portion 362 is shown as if it is not crushed yet to show how the paddle 338 moves through space initially occupied by the second portion 362. In use, the second portion 362 would have been collapsed and be located under the fulcrum 352 in FIG. 14.

Collapsing the second portion 362 causes the base 360 to rupture. The base 360 may rupture in a portion of the base that is deflected into a well 363 in the bottom plate 332, whereas the rest of the base 360 is supported by the bottom plate 332 and does not rupture. Optionally, a portion of the base 360 over the well 363 may be scored or otherwise weakened to encourage it to rupture. Optionally, a protrusion such as bead 356 can be added in the second portion 362. The bead 356 moves downwards from the position shown in FIG. 14 and punctures the base 360.

Opening the base 360 over the well 363 creates a pathway between the inside of the rehydration reagent pouch 308 to point A of the lower plate 332. This pathway extends along dilution reagent pathway 354 to the T-junction 314 and as further described above (see also FIG. 13). Moving the paddle 338 further to the left causes the paddle 338 to bend at the fulcrum 352. The paddle 338 crushes the first portion 358 driving the remaining liquid out of the rehydration reagent pouch 308 until the paddle 338 lies flat on the foil base 360. An optional click lock 340 is engaged to hold the paddle 338, which prevents fluid from flowing back into the rehydration reagent pouch 308. Optionally, the distinct second portion 362 may be omitted and/or the fulcrum 352 of the paddle 338 may be omitted, optionally with suitable re-shaping of the rehydration reagent pouch 308 and paddle 338. However, having a distinct portion of the paddle 338 (in this example including the fulcrum 352 and part of the paddle to the right of the fulcrum 352) contact a distinct portion of the rehydration reagent pouch 308 (in this example second portion 362) before the rest of the paddle 338 contacts the rest of the rehydration reagent pouch 308 helps to reliably rupture the base 360 at the intended location and then permit substantially the entire contents of the rehydration reagent pouch 308 to be emptied.

Figure 15:
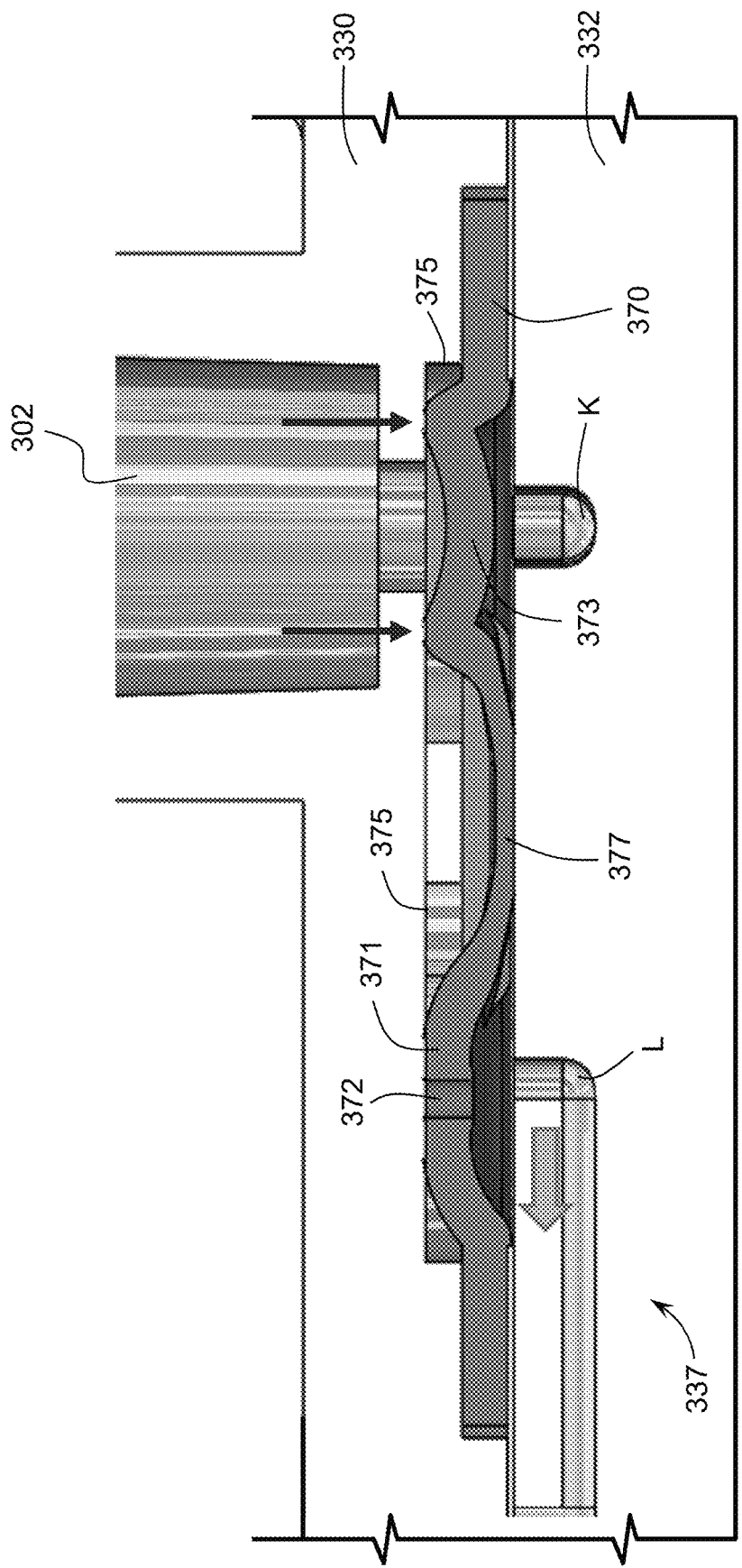
FIG. 15 is a side view of a fill valve.

Referring to FIG. 15, fill valve 337 includes a shaped flap 370 in a chamber 375. In the example shown, the flap 370 is cast from silicone although other materials such as rubber or a flexible plastic may also be used. In the example shown, the chamber 375 is defined by a recess of the top plate 330 and the upper surface of the bottom plate 330. At least a portion of the chamber 375 extending between port 302 and point L is deeper than the thickness of the flap 370 material. However, the flap has a first raised portion 371 and a second raised portion 373. The raised portions 371, 373 are spaced apart from each other by a middle portion 377 of the flap 370 and each fill the depth of the chamber 375. The first raised portion 371 has a hole 372 located over a port in the bottom plate 332 at point L. The second raised portion is located below port 302 in the top plate 330 and over a port in the bottom plate 332 at point K.

Optionally, the second raised portion 373 has a raised ring and an indentation. The raised ring surrounds and seals the bottom of port 302 when no pressure is applied through port 302. The indentation provides a seal over the bottom plate 332 at point K when pressure is applied through the port 302. However, the middle portion 377 of flap 370 may alternatively or additionally prevent flow to point K on the bottom plate 332 when pressure is applied through port 302.

Water injected, for example from a syringe, through the port 302 pushes the raised portions 371, 373 downwards thereby at least partially flattening the flap 370. This creates a path for water to flow from port 302, over the flap 370, through the hole 372 and into a conduit in the bottom plate 332 leading to the extractant channel 304. When water pressure is released, for example by removing the syringe, the flap 370 rebounds and the second raised portion 373 closes the port 302. Later in the process, air from the device 10 pushes water out of the extractant channel 304 back to the fill valve 337. The water from the extractant channel 304 pushes the middle portion 377 of the flap 370 between the raised portions 371, 373 upwards, thereby at least partially flattening the flap 370 while the top of the chamber 375 closes the hole 372 in the first raised portion 371. This creates a path below the flap 370 between points L and K in the bottom plate 332. The water can thereby flow from the extractant chamber 304 through the fill valve 337 to the sample well 316.

In the example of FIGS. 11 to 15, the user moves the paddle 338 but air from the device 10 is used to provide other movements of liquids in the cartridge 300. As described further above, the device 10 performs these and other functions, for example conducting measurements of light emitted in the sample well 316, automatically once the user instructs the device 10 to perform a measurement of the water in the cartridge 300. In other examples, the cartridge 20, 300 or device 10 may contain other devices such as peristaltic pumps or other microfluidic pumps that move and/or meter fluids. In other alternatives, the cartridge 20, 300 can have valves that are activated by solenoids of other moving parts, which may be located in the device 10.

We claim:

1. A cartridge for use with a water testing device, the cartridge comprising,
    a water sample inlet port;
    a sample well in communication with the inlet port; and,
    one or more ATP assay reagents including luciferase, wherein the luciferase is pre-loaded into the sample well;
    and a metering channel in communication with the water sample inlet port and the sample well,
    wherein the cartridge is pre-loaded with ATP.

2. The cartridge containing luciferase of claim 1 wherein the luciferase is in dried form.

3. The cartridge of claim 1 comprising a fill valve adapted to selectively permit flow from the water sample inlet port to the metering channel, or from the metering channel to the sample well.

4. The cartridge of claim 1 comprising an air port in communication with the metering channel.

5. The cartridge of claim 1 comprising a lysing reagent pre-loaded into the metering channel, optionally in a dried form.

6. The cartridge of claim 1 comprising a rehydration and/or dilution reagent in communication with the sample well.

7. The cartridge of claim wherein the ATP is in a stabilized aqueous or dried form.

8. The cartridge of claim 1 wherein the ATP is located in a channel located between an air port and the sample well.

9. The cartridge of claim 8 wherein the ATP channel is in communication with a lock wick.

10. The cartridge of claim 1 comprising a rehydration and/or dilution reagent in communication with the sample well and the ATP.

11. The cartridge of claim 1 comprising one or more reservoirs each containing one or more reagents.

12. The cartridge of claim 11 wherein the one or more reagents are selected from the list consisting of a lysing reagent, a dilution and/or rehydrating reagent, and a calibration reagent.

13. A water testing device in combination with a cartridge of claim 1, wherein the device contains one or more physical, electronic and/or mechatronic devices that interact with cartridge.

14. The device of claim 13 having a light sensor, wherein the light sensor is adapted to receive light generated in the sample well of a cartridge inserted into the device.

15. The device of claim 13 having an air pump.

16. A cartridge for use with a water testing device, the cartridge comprising,
    a water sample inlet port;
    a sample well in communication with the inlet port; and,
    one or more ATP assay reagents including luciferase, wherein the luciferase is pre- loaded into the sample well;
    a metering channel in communication with the water sample inlet port and the sample well; and,
    one or more reservoirs each containing one or more reagents, the one or more reservoirs including at least one collapsible reservoir.

17. The cartridge of claim 16 comprising a paddle adapted to collapse the at least one collapsible reservoir.

18. A water testing device in combination with a cartridge, wherein the cartridge comprises,
    a water sample inlet port;
    a sample well in communication with the inlet port; and, one or more ATP assay reagents including luciferase, wherein the luciferase is pre-loaded into the sample well;

a metering channel in communication with the water sample inlet port and the sample well; and, one or more reservoirs each containing one or more reagents wherein the device contains one or more physical, electronic and/or mechatronic devices that interact with cartridge, and wherein the device is configured to collapse at least one of the reservoirs of the cartridge upon insertion of the cartridge into the device.

19. A process for testing water comprising the steps of, loading water into a cartridge, wherein the cartridge is pre-loaded with one or more ATP assay reagents including at least one ATP assay reagent in solution in a reservoir;

loading the cartridge into a device; and, reacting at least some of the water in the cartridge according to a firefly assay reaction including the one or more pre-loaded ATP assay reagents;

measuring light produced in the cartridge due to the firefly assay reaction from a sensor of the device; and, moving one or more fluids within the cartridge by (a) air pumped from the device into the cartridge and (b) collapsing the reservoir of the cartridge.

20. The process of claim 19 comprising contacting at least some of the water sample in the cartridge with a cell lysing reagent pre-loaded in the cartridge.

21. The process of claim 19 comprising re-hydrating the one or more ATP assay reagents before reacting them with the water sample.

22. The process of claim 19 comprising metering a selected volume from the water loaded into the cartridge for use in the firefly assay reaction.

23. The process of claim 19 comprising moving one or more fluids within the cartridge with air provided from the device through a multiple port valve of the device.

24. The process of claim 19 comprising measuring light produced in the cartridge from ATP pre-loaded in the cartridge.

25. A cartridge for use with a water testing device, cartridge comprising, a water sample inlet port;

a sample well in communication with the inlet port; one or more ATP assay reagents; and, a collapsible reservoir associated with a paddle, wherein the paddle is hinged to the cartridge and is bendable at a fulcrum, and the collapsible reservoir has a region that can be engaged by the fulcrum of the paddle.

26. The fluidic cartridge of claim 25 configured such that a portion of the base of the reservoir below the region is ruptured by movement of the paddle.

27. A cartridge for use with a water testing device, cartridge comprising, a water sample inlet port;

a sample well in communication with the inlet port; one or more ATP assay reagents; and, a fluid valve, the fluid valve comprising a formed resilient flap in a chamber, wherein the chamber is deeper than the flap, wherein the flap has first and second spaced apart raised portions, a hole in the first spaced apart raised portion, wherein one side of the chamber has a port over the second raised portion, and the other side of the chamber has a port under the first raised portion and a port under the second raised portion.

* * * * *